(12) United States Patent
Osterberg

(10) Patent No.: US 6,983,751 B2
(45) Date of Patent: Jan. 10, 2006

(54) CONDOM

(76) Inventor: Brian J. Osterberg, P.O. Box 42, Petoskey, MI (US) 49770-0042

( * ) Notice: Subject to any disclaimer, the term of this patent is extended or adjusted under 35 U.S.C. 154(b) by 0 days.

(21) Appl. No.: 10/712,217

(22) Filed: Nov. 13, 2003

(65) Prior Publication Data

US 2004/0099274 A1 May 27, 2004

Related U.S. Application Data

(60) Provisional application No. 60/428,557, filed on Nov. 22, 2002.

(51) Int. Cl.
*A61F 6/04* (2006.01)

(52) U.S. Cl. ........................ 128/844; 128/842; 128/918; 604/346; 604/347; 604/355

(58) Field of Classification Search ................ 128/842, 128/844, 918; 604/346, 347, 349, 355
See application file for complete search history.

(56) References Cited

U.S. PATENT DOCUMENTS

| | | | |
|---|---|---|---|
| 2,586,674 A | | 2/1952 | Lonne ........................ 128/294 |
| 3,659,599 A | * | 5/1972 | McLaughlin ................. 602/58 |
| 3,809,090 A | * | 5/1974 | Povlacs et al. ............. 604/347 |
| D252,949 S | | 9/1979 | Okamoto ..................... D24/99 |
| 4,919,149 A | * | 4/1990 | Stang .......................... 128/842 |
| 5,109,871 A | * | 5/1992 | Thornton ..................... 128/844 |
| 5,395,674 A | * | 3/1995 | Schmidt et al. ............. 428/178 |
| 5,836,308 A | | 11/1998 | Alla et al. ................... 128/844 |
| 5,885,205 A | * | 3/1999 | Kassman ...................... 600/38 |
| 6,000,398 A | | 12/1999 | Alla et al. ................... 128/844 |
| D420,127 S | | 2/2000 | Rudge et al. .............. D24/105 |
| D448,471 S | | 9/2001 | Johannsson ................. D24/105 |
| 6,308,708 B2 | | 10/2001 | Strauss et al. .............. 128/842 |
| 6,651,667 B2 | * | 11/2003 | Osterberg ................... 128/844 |

FOREIGN PATENT DOCUMENTS

| | | |
|---|---|---|
| JP | 04210056 A | 7/1992 |
| JP | 07250858 A | 10/1995 |
| WO | WO 97/30668 | 8/1997 |

* cited by examiner

*Primary Examiner*—Henry Bennett
*Assistant Examiner*—Camtu Nguyen
(74) *Attorney, Agent, or Firm*—Gifford, Krass, Groh, Sprinkle, Anderson & Citkowski, P.C.

(57) ABSTRACT

An improved condom includes a body that has a wall, a closed end and an open end. The wall of the condom has an interior surface and an exterior surface. A textured portion on the condom functions to increase the sensation transmitted by the condom during use. The textured portion may be positioned in a curved region of the condom. When used as a female condom, the textured portion inhibits the possibility of the condom be displaced. A retention device is also provided that is disposed in the interior of the condom and expands during use.

17 Claims, 3 Drawing Sheets

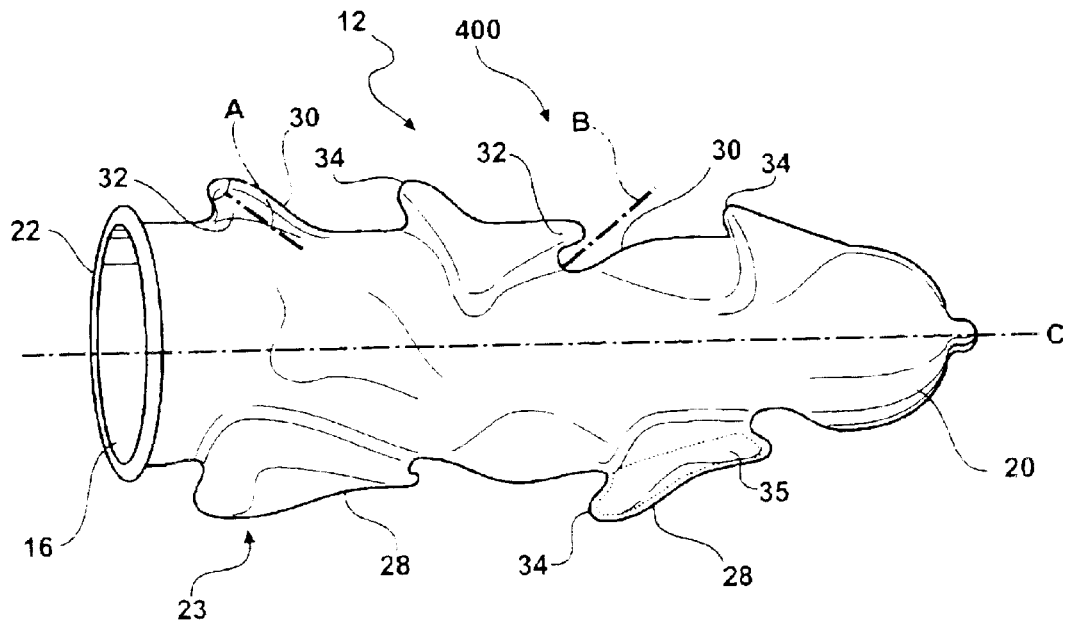
FIG - 2B
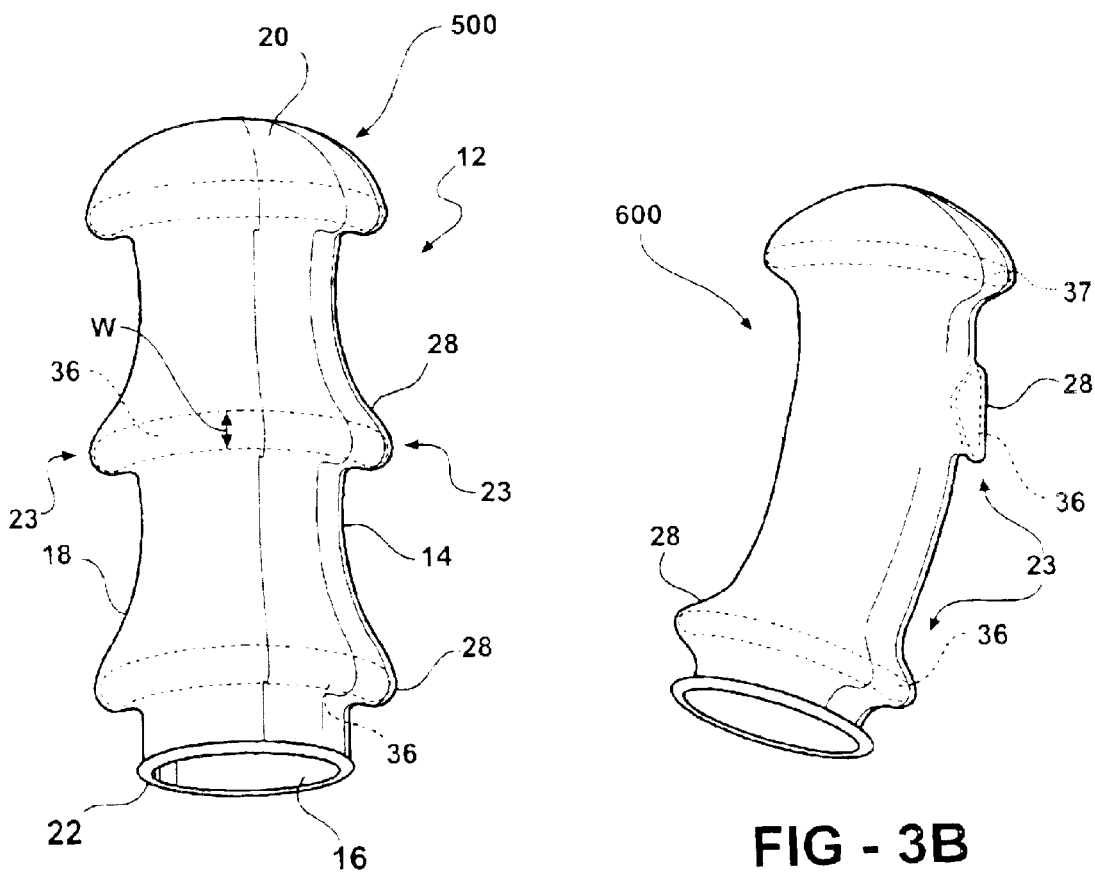
FIG - 3A
FIG - 3B

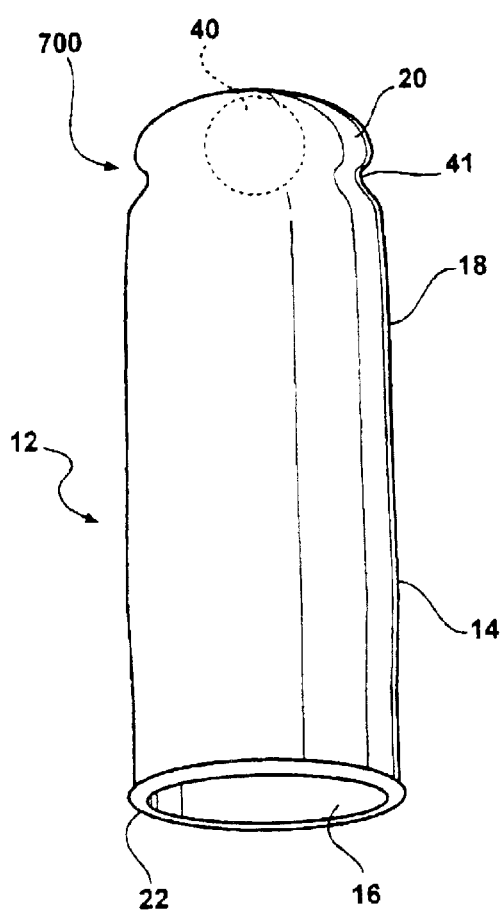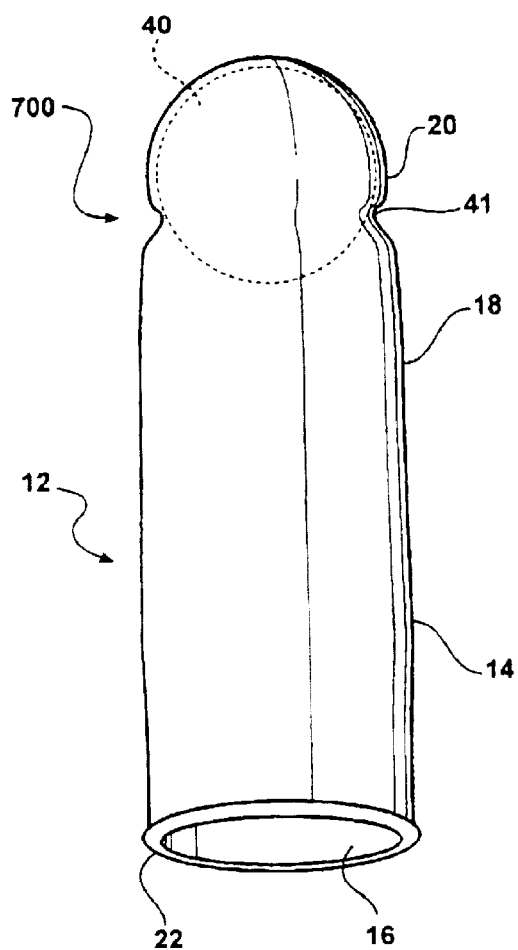
FIG - 4A  FIG - 4B
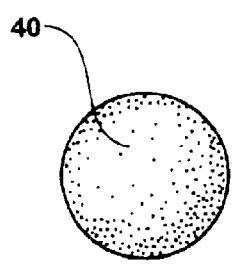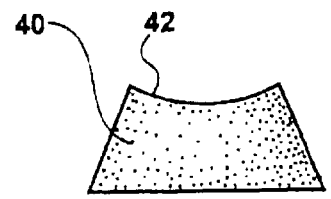
FIG - 4C  FIG - 4D

CONDOM

CROSS-REFERENCE TO RELATED APPLICATIONS

This application claims priority from U.S. Provisional Application No. 60/428,557, filed Nov. 22, 2002.

BACKGROUND OF THE INVENTION

1. Field of the Invention

The present invention concerns an improved condom. More particularly, the invention concerns an improved male or female condom that has an improved shape, surface texturing and a system for anchoring/retaining the condom.

2. Reference to Related Art

Male and female condoms typically include an elongated sheath that has an open end and a closed end. However, from this basic design the prior art has seen a number of advancements. For example, WO 97/30668 shows a male condom that is designed to loosely fit around the user. The wall of the condom includes a series of three to five grooves that are approximately 0.8 cm wide and 1.0 cm deep. The grooves function as bellows that allow the condom to be placed in a substantially flat condition prior to use. A similar design is also shown in U.S. Design Pat. No. 420,127.

It has also been known to place ribbing on the exterior surface of a male condom. For example, U.S. Pat. No. 6,308,708 discloses a male condom having an exterior surface that includes a plurality of intersecting spiral ribs. The regions of ribbing can be staggered along the exterior surface in order to vary the sensation imparted by the condom. Another ribbed design is shown in U.S. Design Pat. No. 252,949.

Finally, the prior art has also seen the introduction of a number of novelty devices such as the condom disclosed by U.S. Design Pat. No. 448,471. This reference generally discloses a design for a condom having an open end and a closed end, with the closed end having the appearance of a killer whale.

SUMMARY OF THE INVENTION

The present invention concerns an improved condom (male or female). A body of the condom includes a wall that has an interior and exterior surface. The body also has an open end and a closed end. This application claims priority from U.S. Provisional Application No. 60/428,557, filed Nov. 11, 2002, which is incorporated by reference herein in its entirety.

A curved region may be provided along the length of the body. The use of a curved region permits the wall of the condom to "bunch". A texture portions, such as ridges, may be disposed in or along the wall of each curved region. The ridges function to increase the sensation transmitted by the condom during use.

The condom may also include a textured portion without the curved region. These textured portions, i.e., protrusions, are formed in the wall or otherwise extend from the wall of the condom. The protrusions may have sloped surfaces that extend in any direction, but are preferably sloped against the direction of insertion. The protrusions may also extend circumferentially around the entire body.

An insert(s) may be positioned in and be operable to engage the interior surface of the body to provide support for each protrusion. The insert(s) may be constructed of any rigid or semi-rigid material, (e.g., a plastic, foam or sponge) may be any size and arranged in a variety of shapes (e.g., oval, triangular, squared, etc.).

Finally, the condom may include a retention device that is positioned within the interior of the body proximate the closed end. The retention device is preferably a sphere of material that is operable to expand following the insertion of the condom such that the exterior surface of the wall of the condom is frictionally secured in position.

BRIEF DESCRIPTION OF THE DRAWINGS

A better understanding of the present invention will be had upon reference to the attached drawings wherein like reference numerals refer to like parts throughout and wherein:

FIGS. 2A–B are side views of alternative embodiments of an improved male condom;

FIGS. 3A–B are a side views of two embodiments of an improved female condom;

FIGS. 4A–B are a side views of an alternative embodiment of a male or female condom;

FIGS. 4C–D show artificial head-like or retention devices that may be incorporated into the male or female condoms of FIGS. 4A–B.

DETAILED DESCRIPTION

The present invention concerns an improved condom that includes a sheath-like body having a wall with an interior and an exterior surface, a closed end and an open end. A textured portion is provided in the wall such that exterior surface has a unique shape and feel.

Figure 1A:
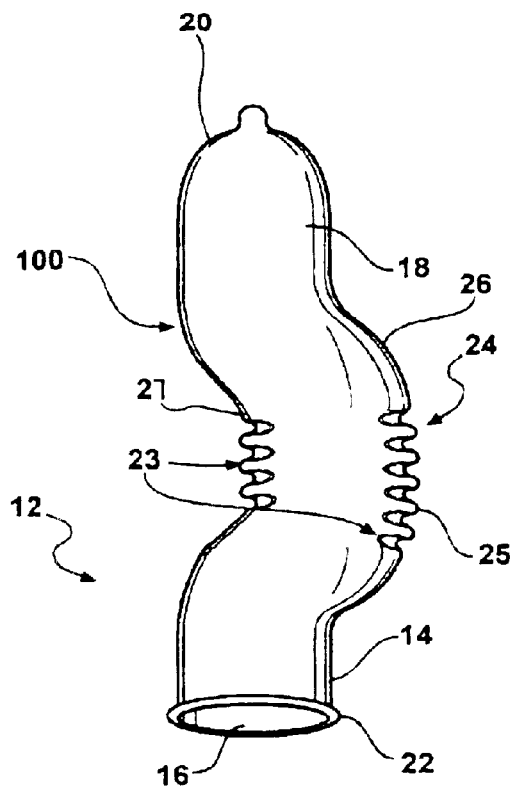
FIGS. 1A–B are side views of two embodiments of an improved male condom.
Figure 1B:
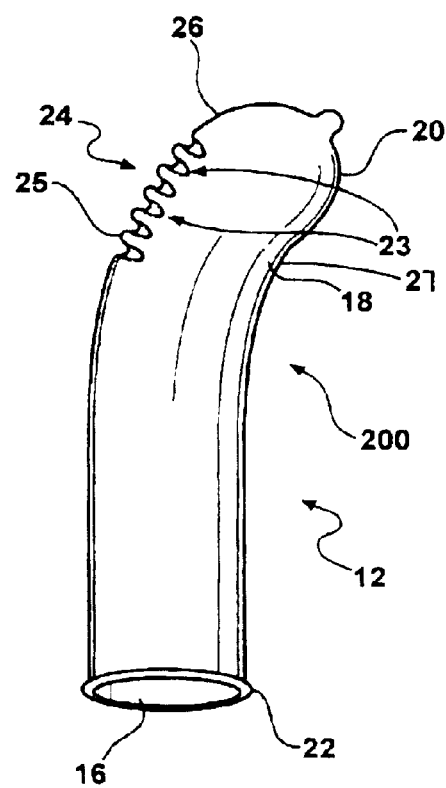

Referring now to FIGS. 1A and 1B, there are shown two embodiments of condoms 100, 200 in accord with the present invention. Like structures will be referred to by like references numbers. The condoms 100, 200 are male condoms that each have a sheath-like body 12 that includes a wall 14 with an interior 16 and exterior 18 surface, a closed end 20 and an open end 22. A curved region 24 is provided along the length of the body. As best shown in FIG. 1B, the curved region 24 is positioned proximate the closed end 20 of the body 12. However, the condoms 100, 200 (and 300, 400) may also be constructed such that the curved region 24 is disposed at any point along the length of body 12. For example, as shown in FIG. 1A, the curved region 24 of the condom 100 is positioned at a point approximately equidistant from the ends 20, 22 of the condom 100. As discussed below, the use of a curved region 24 permits the wall 14 to "bunch" when applied to an erect penis. Textured portions 23, such as ridges 25 (or a pouch on pouch structure), may be disposed in the wall 14 along an inside 27 of each curved region 24. Alternatively, the textured portions 23 may be disposed on an area of the body 14 that is opposite the inside 27 of the curved region. It will also be appreciated that the other areas of the condom 100, 200 may also include one or more textured regions. The ridges 25 function to increase the sensation transmitted by the condom 100, 200 during use.

Still referring to FIGS. 1A and 1B, the condoms 100, 200 are manufactured using an appropriately shaped mold (e.g., a curved condom mold (not shown)). In use, the curved region 24 causes the wall 14 of the body 12 to "bunch" in the area of the curved region 24. The amount of bunching, and thus the sensation being conveyed, depends upon the physical characteristics of a user and the curved shape of the condom and will change from user to user. By way of example when considering condom 200 shown in FIG. 1B, a normally straight human penis could cause significant bunching (or gathering) of the material in the inside 27 of each curved region 24 of the wall 14. The condoms 100, 200 may also convey a different feel, for variety, upon each application since the curved region 24 of the condoms 100, 200 may be positioned differently during use. Additionally, when the curved region 24 is disposed proximate the closed end 20 of the body 12, it is possible that little or no bunching of the wall 14 will occur.

Figure 2A:
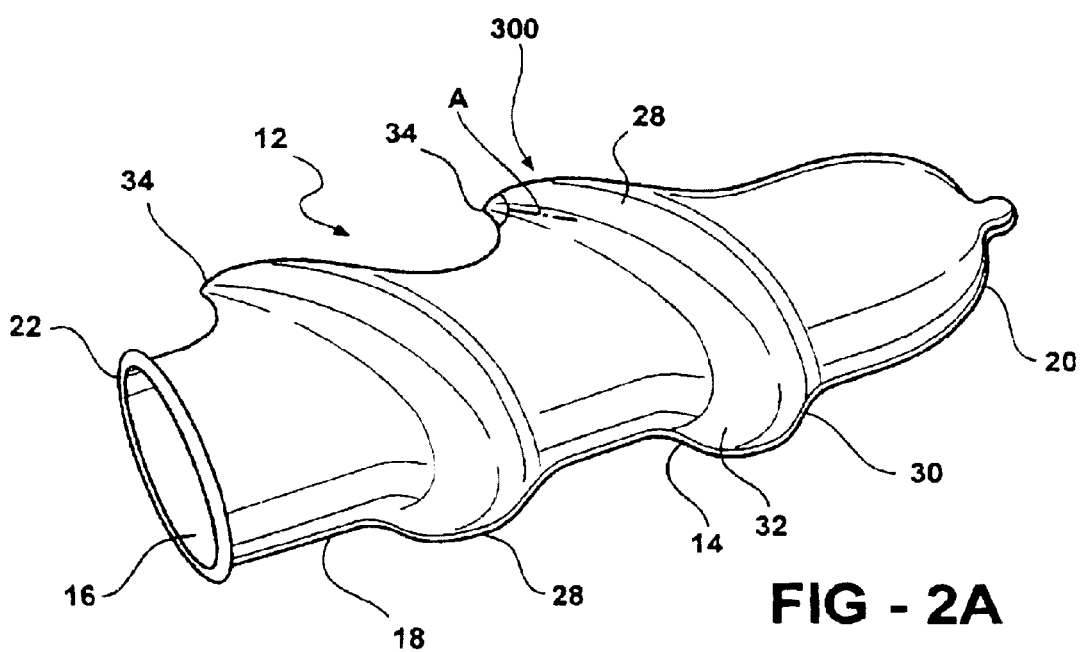

Referring now to FIGS. 2A and 2B, there are shown two alternative embodiments of an improved condom 300, 400 that include a sheath-like body 12 having a wall 14 with an interior 16 and exterior 18 surface, a closed end 20 and an open end 22. The textured portion 23 includes protrusions 28 that are formed in the wall 14 or other otherwise extend from the wall 14. Each protrusion 28 has a generally triangular shape that includes a long sloped surface 30 and a short sloped surface 32 that are joined at an apex 34. The inside angle of the apex 34 between the two sloped surfaces is an acute angle "A" between 0 and 90 degrees. A second acute angle "B" between 0 and 90 degrees is formed at the intersection between the short-sloped surface 34 and the exterior surface 18 of the body 12. The protrusions 28 are spaced along the exterior surface 18. The protrusions 28 may be of any width on the circumference of the pouch and sloped in any direction, but are preferably sloped against the direction of insertion (i.e., toward the open end 22 of the body 12). The protrusion 28 may also extend circumferentially around the entire body 12.

In use, the protrusions 28 create resistance to the withdrawal/extraction of the condom 200 (or alternatively resistance to insertion depending on the slope of the protrusion 28) and also create increased friction between a user and his partner. The protrusions 28 are preferably molded from a flexible material (e.g., latex) as part of the wall 14, but may also extend from the wall 14. Alternatively, the protrusions 28 may be manufactured such that the walls have an increased thickness that imparts a rigid or textured feel to the protrusions 28. The protrusions 28 may be filled with a material 35. Suitable materials 35 include a fluid (e.g., a gel or saline) or a rigid or semi-rigid material (e.g., a polymer, foam or sponge).

The protrusions 28 may be reversible (i.e., may be turned inside out) and may extend inwardly or outwardly relative to a longitudinal axis C of the body 12 of the condom 200. The protrusions 28 may also have a reciprocal movement such that during application and use the protrusions 28 move inwardly and outwardly. Inwardly extending protrusions 28 function to lift and support the interior surface 16 of the wall 14 away from the skin of the user such that contact between the skin and the surface 16 is limited. The lifting of the wall 14 away from the skin of the use also creates an artificial sense of increased circumference of the penis shaft and relieves a user from the "tightly bound" feeling that can be attributed to tight fitting condoms.

Referring now to FIGS. 3A–B, there is shown two embodiments of an improved female condom 500, 600 that includes a sheath-like body 12 having a wall 14 with an interior 16 and exterior 18 surface, a closed end 20 and an open end 22.

As with the disclosure of FIGS. 2A–B, the embodiments of the condoms 500, 600 shown in FIGS. 3A–B include textured portions 23, in the form of protrusions 28, are disposed along the wall 14 of the body 12. An insert 36 is positioned in and engages the interior surface 16 of the body 12 to provide support for each protrusion 28. The insert(s) 36 is preferably a ring-shaped sponge having a diameter between $\frac{1}{64}^{th}$ inch and 4 inches and a width "W" between $\frac{1}{64}^{th}$ (i.e., similar to a very thin gauge wire) and 4 inches. However, the insert 36 may be constructed of any rigid or semi-rigid material, (e.g., a plastic, foam or sponge) may be any size and arranged in a variety of shapes (e.g., oval, triangular, squared, etc.).

Still referring to FIGS. 3A–B, the insert(s) 36 is positioned in the interior of the condom 500, 600 during manufacture by being molded into slots in the inner surface 16 of the wall 14 of the body 12. Alternatively, the insert(s) 36 may be placed into the wall 14 mechanically, e.g., during the latex dipping (or plastic blowing, depending on condom material) procedure of manufacturing the body 12.

By engaging and supporting the protrusions 28, the insert (s) 36 impart rigidity to the protrusions 28 and thus additional friction during use. This additional friction necessarily prevents accidental pullout of the condoms 500, 600 during use by increasing the adhesion of the outer wall 16 the vaginal walls. The insert(s) 36 also assist in keeping the interior surface 16 of the wall 14 of the body 12 from adhering to the skin of the erect male penis, which also prevents pullout of the condoms 500, 600.

Referring now to FIGS. 4A–D, there are shown further embodiments of a female condom 700 and a condom retention device 40. The condom 700 includes a sheath-like body 12 having a wall 14 with an interior 16 and exterior 18 surface, a closed end 20 and an open end 22. A retention device 40 is positioned within the interior of the body 12 proximate the closed end 20 and may by held in position by indentation 41. Alternatively, the exterior surface of the retention device 40 (or a portion thereof) may include an adhesive that mounts the retention device 40 to the interior 16 of the condom 700.

Still referring to FIGS. 4A–D, and as best shown in FIG. 4C, the retention device 40 may be a sphere or other shape of material (e.g., a disk, oval, square, rectangle, etc.) that is operable to expand following the insertion of the condom 700. More specifically, the device 40 is a dehydrated (or merely compressed) spherical sponge (or other expandable material) that has been compressed such that it has an initial diameter (or shape) equal to or smaller than an interior diameter of the condom 700. Alternatively, the device is sponge that is encapsulated by a film that quickly disintegrates when exposed to a liquid (e.g., silicone lubrication as currently used in male and female condoms) and/or temperatures (i.e., in vivo body temperatures of approximately 98 degrees). As the film disintegrates, the sponge expands to a diameter or width that is greater that the interior diameter of the condom 700. For example the sponge may be constructed to expand to between 2 and 10 times (or more) the compressed size. As best shown in FIG. 4D, the device 40 may be dimensioned to have a concave surface 42 that functions as a finger guide.

During use, following the insertion of the condom 400, the device 40 expands to a diameter greater than the interior diameter of the condom 700 to hold it in place such that the exterior surface 18 of the wall 14 of the condom 700 is frictionally secured inside the vaginal cavity of the female user. By frictionally securing the condom 700 in this manner the possibility of an unintentional pullout of the condom 700 is eliminated or greatly reduced.

Having thus described my invention, various modifications will become apparent to those having skill in the art that do not depart from the scope of the present invention.

For example, it will be appreciated that any improvement shown for use with or within a male condom may also be operable for use in a female condom, and visa-versa.

I claim:

1. A condom comprising a body having a wall, a closed end and an open end, the wall defining a protrusion and including an interior surface and an exterior surface, the protrusion being filled with a material and being formed to include a long sloped surface and a short sloped surface, the long and short sloped surfaces forming an apex having an inside angle between 0 and 90 degrees and the short sloped surface defining at a base opposite the apex an outside angle with the exterior surface between 0 and 90 degrees such that the protrusion is sloped toward the open end of the body to thereby create increased friction and resistance between a user and his partner to the withdrawal of the condom.

2. The condom of claim 1, wherein the protrusion extends circumferentially around the body.

3. The condom of claim 1, wherein the material is a fluid.

4. The condom of claim 3, is taken from the group consisting of a gel and a saline solution.

5. The condom of claim 1, wherein the material is taken from the group consisting of a polymer, a foam and a sponge.

6. The condom of claim 1, where the protrusion is reversible.

7. The condom of claim 1, where the body has a longitudinal axis and the protrusion extends inwardly relative to the longitudinal axis.

8. The condom of claim 1, where the body has a longitudinal axis and the protrusion extends outwardly relative to the longitudinal axis.

9. A condom comprising a body having a wall, a closed end and an open end, the wall including an interior surface, an exterior surface and defining a protrusion, the protrusion being formed to include a pair of opposed ends including a long sloped surface and a short sloped surface, the long and short sloped surfaces of each end forming an apex having an inside angle between 0 and 90 degrees and the short sloped surface of each end defining at a base opposite the apex an outside angle with the exterior surface between 0 and 90 degrees such that the protrusion thereby includes an end that is sloped toward the open end of the body and an end that is sloped away from the open end of the body.

10. The condom of claim 9, wherein the protrusion extends circumferentially around the body.

11. The condom of claim 9, wherein the protrusion is filled with a material.

12. The condom of claim 11, wherein the material is taken from the group consisting of a polymer, a foam and a sponge.

13. The condom of claim 11, wherein the material is a fluid.

14. The condom of claim 13, wherein the fluid is taken from the group consisting of a gel and a saline solution.

15. The condom of claim 9, where the protrusion is reversible.

16. The condom of claim 9, wherein the body has a longitudinal axis and the protrusion extends inwardly relative to the longitudinal axis.

17. The condom of claim 9, wherein the body has a longitudinal axis and the protrusion extends outwardly relative to the longitudinal axis.

* * * * *